United States Patent [19]

Laakso et al.

[11] Patent Number: 5,106,865
[45] Date of Patent: Apr. 21, 1992

[54] RADARIN ANTIINSECTAN METABOLITES

[75] Inventors: Jodi A. Laakso, Iowa City, Iowa; Patrick F. Dowd, Peoria, Ill.; James B. Gloer, Iowa City, Iowa; Donald T. Wicklow, Peoria, Ill.

[73] Assignees: The United States of America as represented by the Secretary of Agriculture, Washington, D.C.; Biotechnology Research & Development Corporation, Peoria, Ill.; University of Iowa Research Foundation, Iowa City, Iowa

[21] Appl. No.: 732,659

[22] Filed: Jul. 19, 1991

[51] Int. Cl.$^5$ .......................................... C07D 209/04
[52] U.S. Cl. .................................... 514/415; 548/490
[58] Field of Search ........................ 548/490; 514/415

Primary Examiner—Mary C. Lee
Assistant Examiner—Joseph K. McKane
Attorney, Agent, or Firm—Arnold, White & Durkee

[57] ABSTRACT

Indole diterpene compounds named "radarin" have been isolated from the sclerotia of the fungus *Aspergillus sulphureus*. The radarins are effective for controlling Lepidopteran insects, and have the structures:

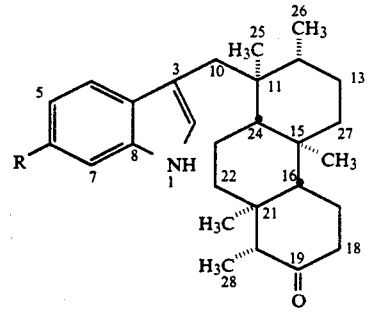

wherein the compound formed when R is a hydroxyl group is designated radarin A and the compound formed when R is a hydrogen atom is designated radarin C; and

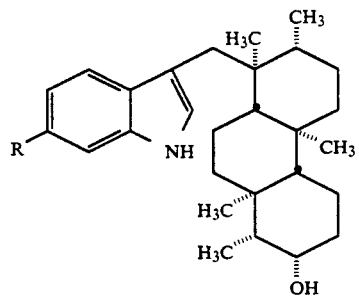

wherein the compound formed when R is a hydrogen atom is designated radarin D and the compound formed when R is a hydroxyl group is designated radarin B.

8 Claims, No Drawings

RADARIN ANTIINSECTAN METABOLITES

BACKGROUND OF THE INVENTION

1. Field of the Invention

The present invention is generally related to indole diterpene compounds. More specifically, the indole diterpene compounds are used as insecticides for control of Lepidoptera species.

2. Background of the Art

Certain fungi produce specialized resting bodies known as sclerotia as a means for surviving adverse environmental conditions which other fungal bodies cannot tolerate, such as harsh climate, nutrient deficiency and desiccation. Generally, sclerotia remain viable in soil for periods of several years, and provide primary inoculum for the producing species when conditions again become favorable for fungal growth. Sclerotia are formed under natural conditions or in solid substrate fermentations, but are not commonly produced in the liquid fermentation cultures generally employed in studies of microbial metabolites. Accordingly, many novel sclerotial metabolites of common fungi such as Aspergillus have not been characterized.

While sclerotia are known to contain biologically active secondary metabolites not found in other fungal parts or in liquid cultures, study of sclerotia as sources of novel metabolites has been limited. Investigation of large sclerotia (ergots) of *Claviceps purpurea* led to the discovery and medicinal use of ergot alkaloids.

Sclerotia have recently been recognized as a valuable potential source for natural antiinsectans. Many sclerotia, which are subjected to predation by fungivorous insects and anthropods during their period of dormancy in soil, have been shown to contain metabolites that exert adverse physiological effects on insects. Gloer et al. [*J. Org. Chem.* 53:5457 (1988)] and Wicklow et al. [*Trans. Br. Mycol. Soc.* 91:433 (1988)] disclose the isolation of four antiinsectan aflavanine derivatives from the sclerotia of *Aspergillus flavus* for use in controlling the dried-fruit beetle *Carpophilus hemipterus* (Nitidulidae:-Coleoptera). TePaske et al. [*J. Org. Chem.* 55:5299 (1990)] disclose a related metabolite, aflavazole, which was isolated from extracts of *A. flavus* sclerotia. Gloer et al. [*J. Org. Chem.* 54:2530(1989)] describe an insecticidal indole diterpene known as nominine found only in the sclerotia of *Aspergillus nomius* for control of the corn earworm *Helicoperva zea* (Leipoptera), formerly *Heliothis zea*. Nominine is also disclosed by Dowd et al. in U.S. Pat. No. 5,017,598 issued May 21, 1991, and entitled "Nominine, an Insecticidal Fungal Metabolite".

There remains a continuing need for new insecticides because many agriculturally important insect species have developed a resistance to the most potent insecticides which are currently available. Moreover, environmentally tolerable replacements for these insecticides are declining. New natural, biodegradable insecticides which are relatively nontoxic to vertebrates and may be produced by fermentation processes are a cost effective replacement for known insecticides.

SUMMARY OF THE INVENTION

In order to satisfy the need for a cost effective, natural, biodegradable insecticide, one aspect of the present invention provides substantially pure indole diterpene compounds. These "radarin" compounds are isolated from the sclerotia of the fungus *Aspergillus sulphureus* and are effective for controlling Lepidopteran insects. The compounds have the structures:

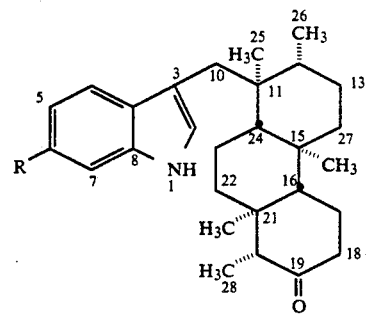

wherein the compound formed when R is a hydroxyl group is designated radarin A and the compound formed when R is a hydrogen atom is designated radarin C; and

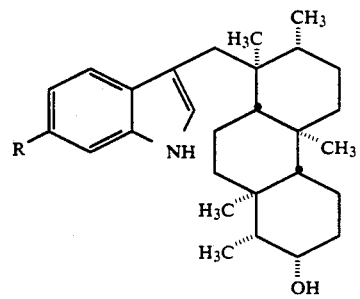

wherein the compound formed when R is a hydrogen atom is designated radarin D and the compound formed when R is a hydroxyl group is designated radarin B.

Another aspect of the present invention provides a composition for controlling insects containing a radarin compound and an inert carrier. The radarin compound is preferably present in the composition in an amount effecting insects of the Lepidopteran species, such as *Helicoverpa zea*. An effective amount of the composition may be applied to a locus of insects in order to control the insects.

DETAILED DESCRIPTION OF THE INVENTION

The present invention provides several substantially pure indole diterpene compounds effective in controlling insects, insecticidal compositions containing a compound of the present invention and a method for controlling insects by applying the compositions to the locus of the insects.

Each indole diterpene compound of the present invention has been designated a "radarin". The radarin compounds, which are effective for controlling Lepidopteran insects, have the structures:

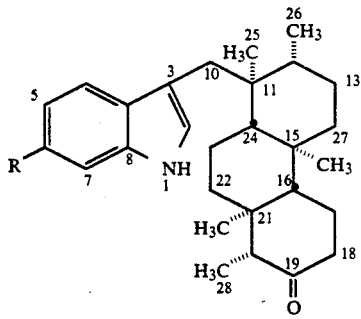

wherein the compound formed when R is a hydroxyl group is designated radarin A and the compound formed when R is a hydrogen atom is designated radarin C; and

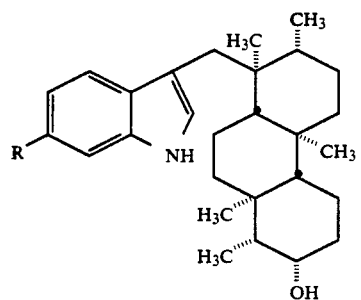

wherein the compound formed when R is a hydrogen atom is designated radarin D and the compound formed when R is a hydroxyl group is designated radarin B.

The radarin compounds are isolated from the sclerotia of the fungus *Aspergillus sulphureus*, a member of the *A. ochraceus* taxonomic group. A strain of the fungus *Aspergillus sulphureus* was deposited on June 11, 1991 in the Agricultural Research Service Patent Culture Collection (NRRL) in Peoria, IL and has been assigned Deposit No. NRRL 18838. The culture deposit will be stored and made available to the public in accord with the provisions of the Budapest Treaty for the Deposit of Microorganisms. All restrictions on the availability of the culture deposit to the public will be irrevocably removed upon the granting of a patent disclosing the strain.

The sclerotia of *A. sulphureus* are produced by solid-substrate fermentation on corn kernels. They are ground by conventional means to a suitable particle size and are extracted with at least one solvent. Suitable solvents for the extraction could be readily determined by the skilled artisan and would include any solvents in which the radarin compounds of the present invention are soluble. Preferably, the ground sclerotia are extracted with pentane and are subsequently extracted with methylene chloride.

Isolation and purification of each radarin compound from the solvent extract is effected by the use of conventional techniques, such as high-performance liquid chromatography (HPLC), thin layer chromatography (TLC), silica gel column chromatography and countercurrent distribution (CCD). In the preferred embodiment of the invention, the solvent extract is separated into fractions by silica gel column chromatography. The fractions of similar composition as determined by TLC are pooled. The resulting fractions are further separated by reversed-phase HPLC to yield pure radarin A as a pink oil, pure radarin B as a yellow solid, pure radarin C as a yellow oil and pure radarin D as a yellow oil. The details of the isolation procedure are described in Example 1, although the procedure is not limited thereto.

Commercial formulations including a radarin compound may be prepared directly from fungal extracts or from the fractions derived from the extracts. However, the formulations are prepared from a pure or a substantially pure radarin when a high degree of specificity is required. For example, if a high degree of predictability of the intended response by both target and nontarget species is required, a formulation prepared from a pure form of a radarin would be used. The formulation would then exclude other substances found in natural fungi which might have an adverse effect on activity or a toxic effect toward nontarget species.

Insecticidal compositions of the present invention include a radarin as described above in combination with a suitable inert carrier as known in the art. Agronomically acceptable carriers such as alcohols, ketones, esters an surfactants are illustrative. A radarin is present in the composition in an amount effecting the target species which is typically at least about 1.0 ppm. The concentration of the radarin compound in an insecticidal composition will vary considerably depending upon the target species, substrate, method of application and desired response. Additional factors to be considered in determining an optimum concentration include phytotoxicity toward the treated plant and the tolerance of nontarget species.

The radarin compounds act to control pests by mechanisms including growth regulation, death inducement, sterilization, as well as interference with metamorphosis and other morphogenic functions. The resulting response is dependant on the pest species, radarin concentration and method of application. The radarin compound is administered in an amount effecting one or more of the responses as may be predetermined by routine testing. Where the intended response is pest mortality, an "effective amount" is defined as the quantity of radarin compound which will effect a significant mortality rate of a test group as compared with an untreated group. The actual effective amount will vary with the species of pest, stage of larval development, nature of the substrate, the type of inert carrier, the period of treatment and other related factors.

The compositions of the present invention are effective in controlling a variety of insects. Agronomically important insects such as those of the order Lepidoptera are of particular interest. However, the compounds and compositions of the present invention are not limited thereto.

The insecticidal compositions of the present invention are used to control insects by applying the composition to the locus of the pest to be controlled. When the radarin compound is intended as a stomach poison, it is applied in conjunction with an inert carrier to the pest diet. The composition is applied to plants by treating the leaf surfaces or by systematic incorporation. As a contact poison, any topical method of application will be effective, such as direct spraying on the pest or on a substrate which is likely to be contacted by the pest.

The following examples are presented to describe preferred embodiments and utilities of the present invention and are not meant to limit the present invention unless otherwise stated in the claims appended hereto.

EXAMPLE 1

ISOLATION AND PURIFICATION OF RADARINS

A culture of *A. sulphureus* (NRRL 18838) was obtained from the Agricultural Research Service (ARS) collection at the USDA Center for Agricultural Utilization Research in Peoria, IL. The sclerotia were produced by solid substrate fermentation of *A. sulphureus* on autoclaved corn kernels using procedures that are described by Wicklow et al., supra (1988). The harvested sclerotia were then ground to a powder with a Tecator mill obtained from Perstorp Instrument Co. before storing at 4° C. until extraction. The ground sclerotia (150.0 g) were extracted using a soxhlet apparatus first with pentane and then with methylene chloride. The methylene chloride extract (1.5 g) was subjected to silica gel column chromatography, using a stepwise gradient from 0-10% (v/v) methanol in chloroform. Fractions of similar composition as determined by TLC were pooled. The resulting active fractions were separated further by reversed-phase HPLC (5-μm Beckman Ultrasphere ODS column; 250×10 mm; UV detection at 215 nm; flow rate 2.0 ml/min) using various methanol-water mixtures to yield 15.1 mg of radarin A, 37.2 mg of radarin B, 8.0 mg of radarin C and 4.4 mg of radarin D.

In determining the properties of the radarin compounds, heteronuclear multiple bond correlation (HMBC) and $^1$H NMR data were obtained on a Bruker AMX-600 spectrometer, while $^{13}$C NMR data were obtained using Bruker AC-300 or WM-360 spectrometers. Heteronuclear multiple quantum correlation (HMQC) experiments were conducted on MSL-300 or AMX-600 spectrometers. Chemical shifts were recorded in acetone-d$_6$ using the corresponding solvent signals (2.04 ppm for $^1$H and 29.8 ppm for $^{13}$C) as references. Distortionless enhancement by polarization transfer (DEPT) experiments were used to determine carbon multiplicities, which are in agreement with the carbon assignments. Long-range CH correlations were established using either the HMBC experiment optimized for $^nJ_{CH}=8.3$ Hz and/or selective insensitive nuclei enhanced by polarization transfer (INEPT) experiments optimized for $^nJ_{CH}$ values of 4, 7, or 10 Hz.

Radarin A was isolated as a pink oil with the following properties: $[\alpha]_D+11.1°$ (c 0.005, CHCl$_3$); HPLC retention time, 25.5 min (88:12 MeOH—H$_2$O); UV (MeOH) 210 (e 6222), 226 (6985), 290 (1512); CD (MeOH) 290 nm ($\Delta\epsilon$-78.6), 233 (−31.9), 216 (−34.3); IR 3404, 2954, 2928, 2855, 1694, 1529, 1453 cm$^{-1}$; $^1$H and $^{13}$C NMR data in Tables 1 and 2, respectively; HMBC and nuclear overhauser enhancement/exchange spectroscopy (NOESY) data in Table 3; electron impact mass spectrometry (EIMS) (70 eV) 421 (M$^+$; rel. int. 4.3), 189 (4.2), 175 (2.6), 161 (3.7), 146 (100), 123 (6.6), 121 (9.3), 119 (5.8), 109 (8.0), 107 (9.0), 105 (7.0); high resolution electron impact mass spectrometry (HREIMS), obsd. 421.2996; calcd. for C$_{28}$H$_{39}$NO$_2$, 421.2981.

Radarin B was isolated as a yellow solid with the properties: mp 115°-118° C. (dec.); $[\alpha]_D+39.4°$ (c 0.003, CHCl$_3$); HPLC retention time, 22.2 min (86:14 MeOH—H$_2$O); CD (MeOH) 228 nm ($\Delta\epsilon$−64.2); IR 3400, 2927, 2876, 1703, 1628, 1453, 1384 cm$^{-1}$; $^1$H and $^{13}$C NMR data in Tables 1 and 2, respectively; EIMS (70 eV) 423 (M$^+$; rel. int. 1.3), 405 (3.8), 243 (7.7), 163 (11), 147 (100), 121 (19), 107 (22), 91 (28), 81 (22); HRFABMS, obsd. 424.3245; calcd. for C$_{28}$H$_{41}$NO$_2$+H, 424.3215.

Radarin C was a yellow oil with the properties: $[\alpha]_D+6.7°$ (c 0.002, CHCl$_3$); HPLC retention time, 40 min (90:10 MeOH-H$_2$O); CD (MeOH) 290 nm ($\Delta\epsilon$−58.7), 229 (−36.7), 212 (+68.4); IR 3411, 2956, 2927, 1708, 1454, 1384 cm$^{-1}$; $^1$H and $^{13}$C NMR data in Tables 1 and 2, respectively; EIMS (70 eV) 405 (M$^+$; rel. int. 2.0), 137 (2.2), 130 (100), 121 (3.2), 111 (3.3), 109 (3.2), 107 (3.5); HREIMS, obsd. 405.3008; calcd. for C$_{28}$H$_{39}$NO 405.3032.

Radarin D was isolated as a yellow oil with: $[\alpha]_D+31.8°$ (c 0.003, CHCl$_3$); HPLC retention time, 45 min (90:10 MeOH-H$_2$O); CD (MeOH) 228 nm ($\Delta\epsilon$−58.0); IR 3415, 2922, 2856, 1709, 1454, 1356, 1228 cm$^{-1}$; $^1$H and $^{13}$C NMR data in Tables 1 and 2 respectively; EIMS (70 eV) 407 (M$^+$; rel. int. 0.5), 389 (1.7), 163 (4.3), 149 (5.5), 131 (100), 121 (6.9), 111 (7.1), 109 (5.1), 107 (6.9); HREIMS, obsd. 407.3176; calcd. for C$_{28}$H$_{41}$NO 407.3188.

TABLE 1

$^1$H NMR Data for Radarins A-D$^a$

| $^1$H# | Radarin A | Radarin B | Radarin C | Radarin D |
|---|---|---|---|---|
| 2 | 6.89(brs) | 6.88(brs) | 7.13(br s) | 7.08(br s) |
| 4 | 7.36(d; 8.6) | 7.38(d; 8.5) | 7.61(br d; 8.0) | 7.60(d; 8.0) |
| 5 | 6.63(dd; 8.6, 2.2) | 6.61(dd; 8.6, 2.2) | 7.00(ddd; 8.0, 7.0, 1.0) | 6.99(ddd; 7.0, 7.0, 1.0) |
| 6 | — | — | 7.07(ddd; 8.0, 7.0, 1.0) | 7.05(ddd; 7.0, 7.0, 1.0) |
| 7 | 6.78(d; 2.1) | 6.8(d; 2.0) | 7.38(br d; 8.0) | 7.36(d; 8.1) |
| 10a | 2.74(d; 15.1) | 2.75(d; 15.2) | 2.83(d; 15.0) | 2.81(d; 15.2) |
| b | 2.65(d; 15.1) | 2.66(d; 15.1) | 2.76(d; 15.2) | 2.72(d; 15.1) |
| 12ax | 1.57(m) | 1.52(m) | 1.60(m) | 1.57(m) |
| 13ax | 1.39(m) | 1.38(m) | 1.42(m) | 1.38(m) |
| eq | 1.25(m) | 1.21(m) | 1.30(m) | 1.21(m) |
| 14ax | 0.71(m) | 0.58(dm; 3.9) | 0.73(m) | 0.58(ddd; 13.0, 13.0, 3.8) |
| eq | 1.58(m) | 1.58(m) | 1.62(m) | 1.6(m) |
| 16ax | 1.28(m) | 0.64(dd; 11.7, 1.9) | 1.36(m) | 0.62(dd; 12.0, 1.8) |
| 17ax | 1.83(m) | 1.50(m) | 1.87(m) | 1.50(m) |
| eq | 1.54(m) | 1.30(m) | 1.56(m) | 1.30(m) |
| 18ax | 2.22(m) | 1.40(m) | 2.32(m) | 1.40(m) |
| eq | 2.13(m) | 1.76(m) | 2.25(m) | 1.78(m) |
| 19eq | — | 3.62(m) | — | 3.61(dm; 2.6) |
| 20ax | 2.10(m) | 1.07(m) | 2.09(m) | 1.06(m) |
| 22ax | 1.20(m) | 0.95(m) | 1.22(m) | 0.95(ddd; 12.8, 12.8, 3.7) |
| eq | 1.72(ddd; 12.9, 3.3, 3.2) | 1.76(m) | 1.76(dm; 12.9) | 1.76(m) |
| 23ax | 1.50(m) | 1.45(m) | 1.52(m) | 1.45(m) |
| eq | 1.96(m) | 1.89(dm; 13.5) | 2.0(m) | 1.89(dm; 16.6) |

TABLE 1-continued

| | | ¹H NMR Data for Radarins A–D[a] | | |
|---|---|---|---|---|
| ¹H# | Radarin A | Radarin B | Radarin C | Radarin D |
| 24ax | 1.10(dd; 11.9, 1.9) | 1.04(m) | 1.11(dd; 12.0, 1.8) | 1.03(dm; 1.8) |
| 25 | 0.82(s) | 0.83(s) | 0.88(s) | 0.86(s) |
| 26 | 1.02(d; 6.7) | 1.04(d; 7.5) | 1.08(d; 6.6) | 1.05(d; 6.5) |
| 27 | 0.86(s) | 0.89(s) | 0.91(s) | 0.89(s) |
| 28 | 0.74(d; 6.7) | 0.92(d; 7.2) | 0.78(d; 6.7) | 0.90(d; 7.1) |
| 29 | 0.68(s) | 1.02(s) | 0.72(s) | 1.02(s) |

[a]Data were recorded in acetone-$d_6$ at 600 MHz.

TABLE 2

| | ¹³C NMR Data For Radarins A–D[a] | | | |
|---|---|---|---|---|
| No. | Radarin A | Radarin B | Radarin C | Radarin D |
| 2 | 123.21 | 123.04 | 124.96 | 124.80 |
| 3 | 112.19 | 112.19 | 112.22 | 112.32 |
| 4 | 122.20 | 120.05 | 119.82 | 119.82 |
| 5 | 109.83 | 109.72 | 119.34 | 119.24 |
| 6 | 153.91 | 153.82 | 121.70 | 121.63 |
| 7 | 97.36 | 97.26 | 112.06 | 111.99 |
| 8 | 138.06 | 138.06 | 137.00 | 136.93 |
| 9 | 124.13 | 124.16 | 130.14 | 130.24 |
| 10 | 34.47 | 34.26 | 34.33 | 34.17 |
| 11 | 41.27 | 41.26 | 41.32 | 41.38 |
| 12 | 36.81 | 36.70 | 36.82 | 36.79 |
| 13 | 28.05 | 28.16 | 28.09 | 28.18 |
| 14 | 40.21 | 40.20 | 40.18 | 40.25 |
| 15 | 38.66 | 38.27 | 38.36 | 38.31 |
| 16 | 59.33 | 61.86 | 59.33 | 61.95 |
| 17 | 22.80 | 16.64 | 22.78 | 16.67 |
| 18 | 41.69 | 36.51 | 41.67 | 36.53 |
| 19 | 211.41 | 71.81 | 211.52 | 71.72 |
| 20 | 58.25 | 50.31 | 58.23 | 50.34 |
| 21 | 42.12 | 38.37 | 42.12 | 38.40 |
| 22 | 40.97 | 41.70 | 40.96 | 41.77 |
| 23 | 19.72 | 19.05 | 19.71 | 19.13 |
| 24 | 51.13 | 51.27 | 51.18 | 51.41 |
| 25 | 18.07 | 17.92 | 18.06 | 17.86 |
| 26 | 17.64 | 17.70 | 17.64 | 17.73 |
| 27 | 16.77 | 17.09 | 16.73 | 17.10 |
| 28 | 7.16 | 12.21 | 7.13 | 12.20 |
| 29 | 15.02 | 16.99 | 14.99 | 17.09 |

[a]Data were recorded in acetone-$d_6$ at 75.6 or 90.7 MHz.

The molecular formula of radarin A was established as $C_{28}H_{39}NO_2$ (10 unsaturations) by analysis of HREIMS and ¹³C NMR data. The mass spectrum contained a base peak at m/z 146 characteristic of a hydroxylated indole moiety, and signals for a 1,2,4-trisubstituted aromatic ring were also evident in the ¹H NMR spectrum. The ¹³C NMR spectrum confirmed the presence of eight aromatic carbons, as expected for a hydroxylated indole, including a downfield-shifted (oxygenated) carbon signal at 153.91 ppm. The presence of a ketone functionality was indicated by the signal at 211.41 ppm. As no other carbon signals appeared beyond the aliphatic region, the remaining unsaturations must be accounted for by three additional rings.

Carbon-proton one-bond correlations were made by analysis of an inverse-detected heteronuclear multiple quantum coherence HMQC experiment as described by Bax and Subramanian in J. Magn. Res. 67:565 (1986). Axial and equatorial proton dispositions were proposed on the basis of ¹H-¹H coupling constants when available. The location of the phenol functionality at C-6 and a second substituent at C-3 of the indole were assigned on the basis of homonuclear correlated spectroscopy (COSY) and inverse-detected heteronuclear multiple-bond correlation HMBC data [Bax and Summers, J. Am. Chem. Soc. 108:2093 (1986)], along with comparison of the ¹³C NMR shifts with those of other 6-oxygenated indoles reported by Shamma and Hindenlang, Carbon-13 NMR Shift Assignment of Amines and Alkaloids, Plenum Press: New York, 1979. An isolated methylene unit, two methyl doublets, and three methyl singlets were also evident in the ¹H NMR spectrum. Although the presence of several ethylene subunits could be determined by COSY correlations, unambiguous establishment of complete spin systems based on COSY data alone was hindered by significant overlap of signals in the ¹H NMR spectrum.

Most of the connectivity of radarin A was assigned by interpretation of the HMBC experiment, the data being shown in Table 3. Linkage of the isolated methylene (C-10) to C-3 of the indole moiety was straightforward, as the two corresponding protons were the only aliphatic signals to show correlations to any aromatic carbons (i.e. to C-2, 3 and 9). The only other cross-peaks for these protons corresponded to carbons 11, 12, and 24. Since the methyl singlet for C-25 correlates with C-10 as well as C-11, 12, and 24, carbons 10 and 11 could be connected. The upfield-shifted methine proton signal at 1.10 ppm (attached to C-24) was well resolved and provided several key correlations. Connection of C-24 to C-11 was confirmed by correlations of H-24 to both C-11 and C-25. The ethylene unit comprising carbons 22 and 23 could be attached to C-24 based on COSY correlations. Carbon-21 was linked to C-22 because the methyl proton singlet at 0.68 ppm ($H_3$-29) showed HMBC correlations to both C-21 and C-22. The well-resolved nature of the downfield-shifted signals of the protons alpha to the carbonyl group allowed for assignment of the unit comprising carbons 16-21 based on the COSY, HMBC, and HMQC data. Moreover, observation of a HMBC correlation between the $H_3$-29 proton signal and the methine carbon C-16 revealed the linkage of C-16 to C-21 to form a six-membered ring. Since the methyl singlet at 0.91 ppm ($H_3$-27) correlated with only one quaternary carbon (C-15) and with C-16, both the methyl group and C-16 must be attached to C-15. The same methyl proton signal also showed a correlation with C-24 and C-14 allowing connections to be made between C-15 and C-24 and between C-15 and the ethylene unit consisting of C-13 and C-14. The methyl proton doublet at 1.02 ppm ($H_3$-26) was correlated to both C-11 and the other carbon of the C-13 -C-14 ethylene unit (C-13), thus completing the gross structure of radarin A and permitting its assignment.

TABLE 3

| HMBC and NOESY Data for Radarin A* | | |
|---|---|---|
| H# | HMBC Correlations | NOESY Correlations |
| 2 | 3, 8, 9 | 10a, 23eq, 24ax, 26 |
| 4 | 3, 6, 8 | 10b |
| 5 | 6[a], 7, 9 | |
| 7 | 5, 6, 9 | |
| 10a | 2, 3, 9, 11, 12 | 2 |
| 10b | 2, 3, 9, 11, 12, 24 | 4, 25, 26 |
| 13ax | 12[b], 14[b], 26[b] | 25, 27 |
| 16ax | | 20ax, 24ax |

TABLE 3-continued

HMBC and NOESY Data for Radarin A*

| H# | HMBC Correlations | NOESY Correlations |
|---|---|---|
| 17ax | 15$^a$, 16$^a$, 18$^a$, 19$^a$, 21 | |
| 18ax | 16, 17, 19 | |
| 18eq | 16, 17, 20 | |
| 20ax | 16, 19, 21, 22, 28, 29 | 16ax, 18ax, 22ax |
| 22ax | 20$^b$, 21$^b$, 23$^b$, 29$^b$ | 20ax, 24ax |
| 22eq | 16, 21, 23$^b$, 24, 29 | 28, 29 |
| 23eq | 11$^a$, 15$^a$, 21$^a$, 24$^a$ | 2 |
| 24ax | 10$^b$, 11, 14$^b$, 15, 16$^b$, 22$^a$, 23, 25, 27 | 2, 16ax, 22ax |
| 25 | 10, 11, 12, 24 | 10b, 13ax, 26, 27 |
| 26 | 11, 12, 13 | 2, 10b, 25 |
| 27 | 14, 15, 16, 24 | 25, 29 |
| 28 | 19, 20, 21 | 22eq, 29 |
| 29 | 16, 20, 21, 22 | 22eq, 27, 28 |

*Data were recorded in acetone-$d_6$. All HMBC and/or selective INEPT correlations represent 2- or 3-bond couplings. NOESY correlations between scaler-coupled protons were omitted. $^a$Correlation observed only in selective INEPT experiments. $^b$Correlation observed only in the HMBC experiment.

Further studies of the same extract led to the isolation of three closely related analogs of radarin A. The mass spectrum of radarin B has the same base peak as radarin A, but indicated a molecular weight two mass units higher. The expected molecular formula of $C_{28}H_{41}NO_2$ was confirmed by HREIMS. The $^{13}C$ NMR spectra of radarins A and B are very similar. The absence of the ketone signal at 211.41 and the appearance of a new signal at 71.81 suggest that radarin B has a secondary hydroxyl group in place of the ketone functionality. The $^{13}C$ NMR shifts for the carbons of radarin B are virtually identical to those of radarin A ($\pm 1$ ppm) except for those alpha and beta to the oxygenated carbon as shown in Table 2. The two alpha carbons, C-18 and C-20, shift from 41.69 and 58.25 in radarin A to 36.51 and 50.31 in radarin B. The three carbons beta to the site of oxygenation are shifted from 22.80 to 16.64, from 42.12 to 38.37, and from 7.16 to 12.21 ppm. A small shift (+2.5 ppm) also occurs in C-16. These differences are consistent with the change in $^{13}C$ NMR substituent effects upon replacement of a carbonyl with an hydroxyl group. The structure of radarin B was verified by analysis of COSY data and a series of selective INEPT experiments described by Bax in *J. Magn. Res.* 57:314 (1984). Because overlap in the proton spectrum of radarin B was more severe than in radarin A, additional confirming evidence was sought by chemical interconversion of radarin B and radarin A. Although several sets of oxidation conditions were unsuccessful, radarin A was ultimately reduced to radarin B with L-Selectride.

The two remaining analogs, radarins C and D both yield mass spectra that exhibit a base peak of m/z 130, which is characteristic of a 3-substituted indole moiety. This observation is in accord with the presence of ortho-disubstitution patterns in the $^1H$ NMR spectral data for both compounds as shown in Table 1. Radarin C has the molecular formula $C_{28}H_{39}NO$ as evidenced by HREIMS, while radarin D has two additional hydrogen atoms. The $^{13}C$ NMR spectra of radarins C and A are nearly identical except for the aromatic region as shown in Table 2. The aromatic carbon shifts for radarin C are typical of a 3-substituted indole. Likewise, the $^{13}C$ NMR spectrum of radarin D differs little from the $^{13}C$ NMR spectrum of radarin B except for the indole signals, which are within 0.5 ppm of the $^{13}C$ NMR shifts for the aromatic carbons of radarin C (Table 2). Thus, the structures of radarins C and D were assigned as shown above, differing from radarins A and B only in the absence of a phenolic OH group.

The relative stereochemistry of radarin A was proposed based on analysis of the NOESY data provided in Table 3. All methylene and methine ring protons could be assigned as axial or equatorial by examination of $^1H$-$^1H$ coupling constants. The axial or equatorial dispositions of the methyl groups were decided based on their NOESY interactions with other protons as shown below.

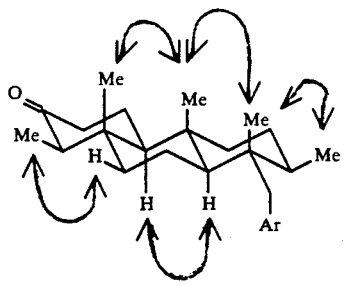

The methyl group attached to C-20 (H$_3$-28) must be in an equatorial position since it has a NOESY interaction with the equatorial proton on C-22. Strong NOESY correlations between H$_3$-29 and H$_3$-27 and between H$_3$-27 and H$_3$-25 indicate 1,3-diaxial interactions. Hence, these three methyl groups must be on the same face of the ring system and in axial positions. Because there is a NOESY correlation between H$_3$-25 and H$_3$-26, H$_3$-26 must be in an equatorial position, making these two methyls cis to each other. The axial methine proton H-24 shows a NOESY correlation with H-16 which also represents a 1,3-diaxial interaction. This 1,3-diaxial association, together with the strong correlation between H$_3$-27 and H$_3$-29 clearly demonstrate that both of the ring fusions in the tricyclic ring system are trans. Other NOESY correlations support the proposed relative stereochemistry as depicted in radarin A. Dreiding molecular models suggest that the three rings must exist in chair conformations. If ring A were in a boat conformation, the methyl group C-26 would be very unlikely to show a NOESY correlation with either proton on C-10, since C-26 and C-10 would be separated by a vicinal angle of nearly 180°. The 1,3-diaxial NOESY interaction between H-22ax and H-24ax suggests that the B ring also must be in a chair conformation. Ring C cannot be in a boat conformation because H-18ax and H-20ax show a strong NOESY correlation (1,3-diaxial relationship). The stereochemistry of the hydroxyl group in radarins B and D must be axial, as the proton on C-19 lacks a large (diaxial)$^3J_{HH}$ value. The remaining stereochemical assignments for radarins B and D were made by analogy to radarin A. A stereoselective reduction of radarin A to radarin B provided further confirming evidence for the stereochemical relationship of radarins A and B.

Because radarins A and C possess substituted cyclohexanone moieties, the circular dichroism (CD) spectra were examined in an effort to propose absolute stereochemistry. The octant rule, as disclosed by Moffitt et al., *J. Am. Chem. Soc.* 83:4013 (1961), relates the sign and amplitude of the Cotton effect for a ketone carbonyl group in a cyclohexanone ring in the chair conformation to the spatial orientation of the atoms near the ketone. Both radarins A and C yield CD spectra with negative differential dichroic absorptions at 290 nm for the ketone carbonylchromophore. Upon projection of the two possible enantiomers into octants (given the proposed relative stereochemistry), the sign of the CD spectrum in the region of the carbonyl absorption suggested that the absolute stereochemistry of the radarins be proposed as shown above. As expected, radarins B and D lack any corresponding absorption.

Reduction of Radarin A to Radarin B

L-Selectride (45 µl of a 1.0M solution in tetrahydrofuran) was added to a 2-ml reaction vial at −78° C. containing 2.0 mg of radarin A in 1.0 ml of dry tetrahydrofuran. After the mixture was stirred for 30 min at −78° C., water (50 µl) was added and the mixture was allowed to warm to room temperature (15 min). Anhydrous magnesium sulfate was added and the solution was then passed through a small silica column. The product obtained upon evaporation of the solvent was redissolved in 1.0 ml methylene chloride and extracted with water (5×1 ml). The organic phase was dried and evaporated to yield radarin B (1.9 mg, 95% yield) which was identical to the natural product based on $^1$H NMR and HPLC analysis.

EXAMPLE 2

Insecticidal Activity of Radarins

The compound was evaluated by insect bioassays described previously by Dowd in *Entomol. Exp. Appl.* 47:69 (1988). Neonate larvae of *H. zea* were used for all assays. They were obtained from laboratory colonies reared on pinto bean-based diet at 27° C.±1° C., 40±10% relative humidity, and a 14:10 light:dark photoperiod.

The diet used to rear the insects was based on a standard pinto bean diet for many species, which contains the following ingredients: 120 g dried pinto beans, 43 g wheat germ, 28 g brewer's yeast, 8 g Vanderzant's vitamin mix, 2.8 g ascorbic acid, 1.75 g methyl paraben, 0.9 g sorbic acid, 12 g agar, 2 ml formaldehyde (38%), 1.5 ml of propionic-phosphoric acid solution (42% propionic acid, 4.2% phosphoric acid), and 550 ml water. All dry diet ingredients (except for the pinto beans) were purchased from U.S. Biochemicals Corp. Before use, the beans were soaked in water until saturated (overnight). The agar was added to 250 ml of water and brought to a boil. The other ingredients were blended in a Waring blender until uniformly mixed. The hot agar was added, and blending continued until all ingredients were uniformly mixed.

The pinto bean-based diet thus prepared was added in 5-ml quantities to test tubes. The test tubes were held at 60° C. until chemicals were incorporated to prevent solidification of the diet. A radarin compound of the present invention was added in 125 µl of acetone to the liquid diet to give a final concentration of 100 ppm. Upon addition of the radarin, the mixture was removed from the water bath. The chemical was incorporated into the diets by blending vigorously with a vortex mixer for 20 sec. Preliminary observations with colored solutions of both water and acetone indicated uniform incorporation by this method. The diets were dispensed into culture plates and allowed to cool to room temperature. To remove the potentially toxic acetone, the diets were placed in a fume hood for ca. 20 min until slight darkening occurred. The diets were cut into approximately equal sections, and each section was placed into a well of a 24-well immunoassay plate. A single neonate *H. zea* was added to each well. To prevent desiccation of the diet, the plate was covered by a sheet of parafilm, a sheet of cardboard, and the plastic cover. The cover was secured by two rubber bands, and groups of plates were placed in two polyethylene bags held closely by rubber bands. The plates were held under the same conditions used to rear the insects. Mortality was checked at 2, 4 and 7 days, and the surviving larvae were weighed after 7 days. Each chemical set was tested on a total of 20 larvae.

Radarin A induces a 52.7% reduction in weight gain relative to controls after one week when incorporated into a standard test diet of the corn earworm *Helicoverpa zea* (formerly *Heliothis zea*) at 100 ppm. Radarin C also exhibits activity at the same concentration, causing a weight gain reduction of 15.8%, while radarin b causes a reduction of 9.6% in this assay at 100 ppm. Further biological evaluation revealed that radarin A is active toward human lung carcinoma A549, breast adenocarcinoma MCF7 and colon adenocarcinoma HT-29 cells with $ED_{50}$ values of 2.5, 5.5 and 1.9 µg/ml, respectively. Radarin B possesses comparable activity in these three cell lines, affording $ED_{50}$ values of 2.0, 2.0 and 0.7 µg/ml, respectively.

EXAMPLE 3

Topical Insecticidal Activity of Radarin A

Neonate larvae of *H. zea* were used for all assays. They were obtained from laboratory colonies reared on pinto bean-based diet at 27° C.±1° C., 40±10% relative humidity, and a 14.10 light:dark photoperiod. A single larva *H. zea* was added to each well of a 24-well immunoassay plate. Each larva was treated with a dosage of 2 µg of radarin A in 0.22 µl acetone per 2 mg larva which was administered from a syringe touching the dorsum of the larva. The larvae were fed the standard pinto bean diet as described in example 2. To prevent desiccation of the diet, the plate was covered by a sheet of parafilm, a sheet of cardboard, and the plastic cover. The cover was secured by two rubber bands, and groups of plates were placed in two polyethylene bags held closely by rubber bands. The plates were held under the same conditions used to rear the insects. Mortality was checked at 4 days, and the surviving larvae were weighed.

Radarin A exhibits significant topical activity against the corn earworm *H. zea*. Administering this compound at 2 µg per 2 mg insect caused a 54.3% reduction in weight gain of the test insects relative to controls.

While the invention is susceptible to various modifications and alternative forms, specific embodiments thereof have been shown by way of example and were herein described in detail. It should be understood, however, that is not intended to limit the invention to the particular forms disclosed, but on the contrary, the intention is to cover all modifications, equivalents, and alternatives falling within the spirit and scope of the invention as defined by the appended claims.

We claim:

1. A substantially pure indole diterpene compound having the structure:

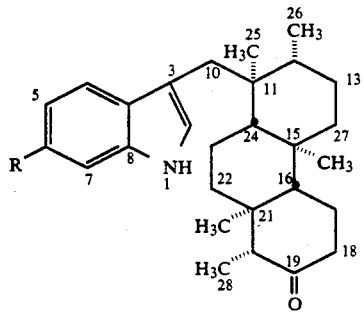

wherein: R is a hydrogen atom or a hydroxyl group, such that the compound formed when R is a hydrogen atom is designated radarin C and the compound formed when R is a hydroxyl group is designated radarin A.

2. A substantially pure indole diterpene compound having the structure:

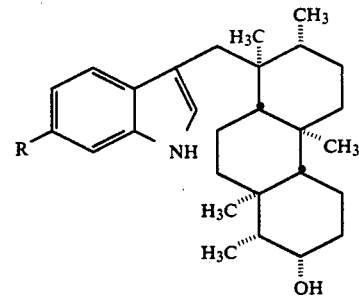

wherein: R is a hydroxyl group, such that the compound formed is designated radarin B.

3. A composition for controlling insects comprising: an insecticide selected from the group consisting of radarin A, radarin B and radarin C; and an inert carrier.

4. The composition of claim 3 including an amount of the insecticide effecting insects of the Lepidoptera species.

5. The composition of claim 3 including an amount of the insecticide effecting *Helicoverpa zea*.

6. A method of controlling insects comprising applying an effective amount of an insecticide selected from the group consisting of radarin A, radarin B and radarin C to a locus of insects.

7. The method of claim 6 wherein the insects are Lepidoptera species.

8. The method of claim 6 wherein the insects are *Helicoverpa zea*.

* * * * *